United States Patent [19]

Wiegand et al.

[11] Patent Number: 4,917,045

[45] Date of Patent: Apr. 17, 1990

[54] SILICON COMPOUNDS IN POULTRY HATCHING

[75] Inventors: Karl E. Wiegand; Patrick C. Hu, both of Baton Rouge, La.

[73] Assignee: Ethyl Corporation, Irvine, Calif.

[21] Appl. No.: 223,020

[22] Filed: Jul. 22, 1988

[51] Int. Cl.⁴ .............................................. A01K 45/00
[52] U.S. Cl. ......................................... 119/1; 514/218
[58] Field of Search ............................ 119/1; 426/532; 427/226; 514/478, 426; 548/341, 371; 623/16, 66

[56] References Cited

U.S. PATENT DOCUMENTS 4,469,047  9/1984  Miller ...................................... 119/1
4,762,829  8/1988  Yamatsu et al. ...................... 514/218

FOREIGN PATENT DOCUMENTS 285285  3/1914  Fed. Rep. of Germany .

OTHER PUBLICATIONS

Carlisle, Chap 4 of *Silicon & Siliceous Structures in Biological Systems*, Simpson T. L., ed. B. E. Springer Verkog, New York (1981), pp. 69–94.

*Primary Examiner*—Richard J. Apley
*Assistant Examiner*—N. Paul
*Attorney, Agent, or Firm*—John F. Sieberth; Robert J. Baran

[57] ABSTRACT

Organic silicon compounds in which silicon is solely bonded to oxygen, fluorine, chlorine or bromine such that not less than one-fourth of the silicon valences are satisfied by bonding to oxygen, stimulate the deposition of bone in bird embryos. Preferred birds are domestic fowl, such as chickens and turkeys. The silicon compounds are administered to the bird eggs by such means as injecting the eggs, or spraying or soaking them.

11 Claims, No Drawings

SILICON COMPOUNDS IN POULTRY HATCHING

CROSS-REFERENCE TO RELATED APPLICATION

Reference is made to Application Ser. No. 123,281, filed Nov. 27, 1987, by Sebastian M. Laurent, for Zeolites in Poultry Hatching. That application pertains to use of different compounds in a method similar to that disclosed herein.

FIELD OF THE INVENTION

This invention pertains to the use of silicon compounds to stimulate deposition of bone. It also relates to the general field of poultry farming, and relates particularly to treatment of poultry eggs to improve hatching characteristics. It also relates to the improved, fertile poultry eggs produced by the method of this invention, and to the improved chicks which hatch from such eggs.

BACKGROUND

Silicon containing reaction products of orthosilicic acid esters and certain polyhydroxy compounds are known, German Patent No. 285,285.

SUMMARY OF THE INVENTION

In a principal aspect, this invention relates to the use of silicon compounds to stimulate the growth of bone tissue in poultry embryos. More particularly, this invention relates to the use of organic silicon compounds to treat fertile poultry eggs, and thereby improve the characteristics of the chicks hatched therefrom. The invention also relates to the improved fertile eggs and improved chicks that are produced by the method of this invention.

Generally speaking, chicks produced by use of this invention are heavier than chickens produced from non-treated eggs of equal weight. Heavier chicks are stronger, and have more vigor, and a greater survival rate than chicks of lesser weight. Heavier hatched chicks grow faster and convert feed more efficiently than smaller chicks. Industry and literature data indicate that 1.9 gram heavier chick translates into a 6 percent heavier broiler at grow-out. This result reduces the grow-out period by 3 days and cost of production by almost 4 percent.

As shown below, silicon-containing agents of this invention stimulate bone tissue production. This causes a greater amount of bone tissue to be produced by embryonic birds, e.g. chickens or turkeys. The increased amount of bone is evident in increased bone weight or length. Thus on average, poultry chicks hatched from eggs treated according to this invention have an increased amount of bone tissue, when compared to chicks hatched from untreated eggs. The increased bone tissue produced by this invention improves the strength or vigor, i.e. hatching characteristics of the chicks which hatch. Thus on average, hatched chicks produced by this invention are of superior quality when compared to birds hatched from untreated eggs.

The therapeutic agents (i.e. bone growth stimulating agents) used in this invention are physiologically acceptable, organic silicon compounds in which the silicon is solely bonded to oxygen or halogen. Of the halogens, fluorine, chlorine and bromine are preferred. In preferred therapeutic agents, not less than one-fourth of the valences of silicon are satisfied by bonding to oxygen. In other words, at least one-fourth (and preferably more) of the silicon valences are satisfied by bonding to oxygen rather than to halogen. As examples of compounds which can be employed in this invention, there are tetraorganoorthosilicates, silicon-containing reaction products derived from carbohydrates such as glycerin, glucose, sucrose, and ascorbic acid, and silicon tetracarboxylates such as silicon tetraacetate.

In a highly preferred embodiment, this invention comprises the use of silicic acid produced—from one or more of the aforementioned therapeutic agents—in a poultry egg which has been treated with one or more of the aforementioned therapeutic agents. The silicic acid produced in this way increases the formation of calcium-related bone in the poultry embryo which has been treated.

The site and degree of hydrolysis which occurs (within the egg or the embryo) with the therapeutic agents of this invention may also serve to alter their specific activities, directing them to systemic locations not typically available to free silicic acid, thereby allowing interaction with new or additional active sites. Thus, not only the parent compounds, but all metabolites thereof, including silicic acid itself, may be involved in particular bone growth stimulatory activity of interest here. We thus recognize that a complex set of transformations in these compounds is expected, and any or several transformation products can be responsible for different spectra of activity or utility.

DESCRIPTION OF PREFERRED EMBODIMENTS

It has been discovered that the addition of a small amount of a specified type of organic silicon compound directly to an egg for hatching a poultry chick, effectively improves the chick. The improvement comprises an increase in bone tissue caused by the bone growth stimulating agent of this invention. Such increase in bone tissue improves the strength or vigor of the chick.

The invention comprises a process for stimulating the deposition of bone in a bird embryo, e.g. a poultry embryo, by directly adding to a fertilized bird egg, prior to hatching of a chick therefrom, a small but effective amount of (i) a physiologically acceptable organic silicon compound in which silicon is solely bonded to oxygen, or fluorine, or chlorine or bromine, such that not less than one-half of the valences of silicon are satisfied by bonding to oxygen, or (ii) silicic acid produced in said egg, from an effective amount of said organic silicon compound administered to said egg.

The amount of physiologically acceptable organic silicon compound which can be administered to the poultry egg generally contains less than about 35 micrograms of silicon. Preferably, from about 2 to about 16 micrograms are added per egg. However, greater or lesser amounts may be used if desired.

The method of treating poultry eggs with a therapeutic compound of this invention is not critical. One method comprises injecting a solution or suspension of the agent into the egg. When this method is used, an amount of solution or suspension—containing the desired amount of silicon—is added to the interior of the egg. For example, the solution or suspension can be injected by a needle into the air space between the chorioallantoic membrane and the shell. Generally speaking, the amount of solution or suspension used is equal to or about 0.1 milliliter. However, greater or lesser volumes can be used if desired. Usually, sterile water suspensions of the bone stimulating agent are injected. After injection, the hole in the egg shell (through which the injection took place) can be sealed with wax, and the eggs set in an incubator and hatched.

Infusion of bone growth stimulating agent into the egg can also be made by spraying or soaking the fertile eggs with a suspension or solution containing the agent. The pore size of chicken egg shells average about 7-9 microns. Hence for chicken eggs, when a suspension of a growth stimulating agent is used, it is preferred that the suspension contain the agent in a smaller particle size, e.g. 3 microns or less.

When suspensions are used for soaking eggs, concentrations of the bone stimulating agent are generally limited to reduce or avoid pluggage of egg shell pores. If too many pores are plugged, death of the embryos can occur upon incubation. To stimulate absorption into the egg, suspensions or solutions of the agents of this invention can be slightly chilled before spraying or soaking the eggs.

For chicken eggs, water suspensions containing 200-500 ppm of the agent are preferred. Higher or lower concentrations can be used, if desired. For example, concentrations of the bone growth stimulating agent of about 50-2000 ppm or higher, e.g. 3000 ppm are suitable. The concentration of the therapeutic agent in water should be sufficiently strong to provide an increase in the amount of bone tissue of the poultry chick, but not be so high as to have a deleterious effect on the chick embryo.

It can be appreciated that the concentrations of bone growth stimulating agent will vary somewhat with the type of poultry egg being treated. Larger eggs generally have a larger pore sizes. Turkey eggs, for example, are usually larger than chicken eggs, and their shells have pores that are much larger in diameter. Thus, when treating turkey eggs the bone growth stimulating agent may be present in particles of a larger size than when treating chicken eggs. The greater number of pores within turkey eggs should be considered when deciding on the concentration of therapeutic agent which is to be utilized.

One type of therapeutic agent employed in this invention is a silicate ester. Preferred silicate esters are the orthosilicates; i.e. compounds having the formula $Si(OR)_4$, wherein R is an organo radical. In this formula, the radicals may be alike or different. Preferably, all four organo radicals in the orthosilicate starting materials are the same. The exact nature, size and configuration of the organo radicals is not critical.

For example, the radicals depicted by R in the above formula, may be solely composed of carbon and hydrogen. Such radicals may be cyclic or acylic. Typically, they are alkyl radicals. Straight or branched chain alkyl groups are suitable. For example, the radicals depicted by R may be alkyl radicals having 1 to about 6 carbon atoms, i.e. "lower alkyl radicals" as defined above. Examples of such radicals are methyl, ethyl, n-propyl, sec-butyl, n-pentyl, n-hexyl, and the like.

Because they are readily available, one type of preferred orthosilicate for use in this invention contain from 4 carbon atoms (i.e. four methyl groups) up to about 24 carbons (four hexyl groups). A highly preferred tetraalkylorthosilicate of this type is tetraethylorthosilicate; $Si(OC_2H_5)_4$.

It is to be understood, however, that other physiologically acceptable substituents may be present in the silicate esters employed in this invention. Such substituents are illustrated by acyl, aryl, aralkyl, alkaryl, heterocyclic alkyl, sulfonyl, alkylsulfonyl, arylsulfonyl, alkylphosphato, carbonyl, thiocarbonyl, and the like.

A second type of therapeutic agent of this invention is similar to the type described above. In the second type, the radical depicted by R in the above formula is a polyhydroxy radical, such as that derived from glycerin or propylene glycol. Thus, this invention comprises the use of glycerol and glycol orthosilicates. The polyhydroxy radical may be derived from other carbohydrates, such as sugars, including aldoses and ketoses, or from alcohols derived therefrom, e.g. mannitol. The following are examples of this type of therapeutic agent: glycerin orthosilicate, mannitol orthosilicate, glucose orthosilicate, fructose orthosilicate, and sucrose orthosilicate. Such materials and related others, may be prepared by the process described in German Pat. No. 285,285, Mar. 22, 1914.

It is to be understood however, that for this invention the nature of the polyhydroxy radical may have a modifying effect but is not critical, and that such radicals can be derived from any physiologically acceptable carbohydrate, including polyhydroxy aldehydes, polyhydroxy ketones, or compounds that can be hydrolyzed to them. Thus, the carbohydrate can be a monosaccharide, disaccharide, oligosaccharide, or a polysaccharide, e.g. starch. The monosaccharides can be a triose, tetrose, pentose, hexose, and so on. Preferred carbohydrates for this invention have up to about 18 carbon atoms.

As shown by the German Patent cited above, therapeutic agents utilized in this invention can be prepared by reacting a tetraloweralkylorthosilicate, such as tetraethylorthosilicate, with an aldose or ketose under conditions which favor transesterification. They may also be prepared from a silicon halide, such as $SiCl_4$ or $SiBr_4$, by reaction with the aldose or ketose in the presence of a base. This method may somewhat rearrange the molecular configuration of the sugar reactant, and may also result in less than all of the halogen atoms being substituted by the aldose or ketose. Nonetheless, these materials can be utilized in this invention. Preferably, at least half of the silicon valences are satisfied by bonding to oxygen instead of halogen.

A third type of therapeutic agent of this invention is a reaction product of ascorbic acid or a substituted ascorbic acid with a tetralkylorthosilicate.

Ascorbic acid has the formula:

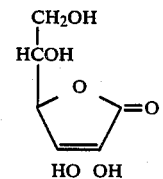

It is a preferred starting material for preparing therapeutic agents of this invention. Substituted ascorbic acids can also be used as starting materials. For the purpose of this invention, the term "substituted ascorbic acids" means those compounds which have the ascorbic acid structure depicted above, with one or more replaceable hydrogens substituted with an organic radical. To be useful as starting materials, the substituted ascorbic acids must have at least one replaceable hydrogen (e.g. a hydrogen in an —OH group) which is reactable with the silicate ester under the reaction conditions employed.

The organo groups which may be present as substituents in the substituted ascorbic acid can be hydrocarbyl groups, i.e. groups that are solely composed of carbon and hydrogen. Preferably, the hydrocarbyl groups are alkyl radicals; more preferably, lower alkyl radicals. For the purpose of this invention, "lower alkyl radicals" are alkyl radicals having up to about 6 carbon atoms. Straight or branched chain alkyl radicals may be present as substituents on the ascorbic acid moiety, and are included in the term "lower alkyl radicals". Examples of such radicals are methyl, ethyl, n-propyl, sec-butyl, n-pentyl, n-hexyl, and the like.

It is to be understood, however, that the nature and size of the organo substituents (which may be bonded to the ascorbic acid moiety) may have a modifying effect, but are not critical so long as they are physiologically acceptable. For the purpose of this invention, "physiologically acceptable" means that the material is not so toxic as to make the silicon compound unacceptable as a therapeutic agent. Preferably, the groups can be added to the ascorbic acid structure at an acceptable cost. Stated another way, it is preferred that the substituent groups be relatively inexpensive. Also, it is preferred that the organo substituents be of a size, nature, and configuration that they do not hinder the desired reaction by steric hindrance, or by causing an unacceptable amount of extraneous side reaction(s). In addition to the hydrocarbyl groups described above, other physiologically acceptable substituents can be present in the ascorbic acid derivative. Such substituents are illustrated by acyl, aryl, aralkyl, alkaryl, heterocyclic alkyl, sulfonyl, alkylsulfonyl, arylsulfonyl, alkylphosphato, carbonyl, thiocarbonyl, and the like.

There is no real upper limit on the number of organic substituents which can be bonded to the ascorbic acid moiety, provided that there is at least one reactable hydrogen present. Generally speaking however, mono-substituted ascorbic acids are preferred over multi-substituted ascorbic acids. Thus, in a highly preferred embodiment, the ascorbic acid derivative used as a starting material for preparing therapeutic agents of this invention contains from 6 to about 12 carbon atoms.

To prepare therapeutic agents of this invention from ascorbic acid or a substituted ascorbic acid, or other carbohydrate of the type described above, one or more ascorbic acid or carbohydrate compounds are mixed with one or more silicate esters, and heated. Preferably, from 1 to 4 moles of ascorbic acid or substituted ascorbic acid or carbohydrate are reacted per mole of silicate ester, or 1 to 4 moles of silicate ester are reacted per each mole of carbohydrate, ascorbic acid or substituted ascorbic acid. Greater or lesser ratios can be used, but use of these ratios may entail the need to separate unreacted starting material from product. Preferred silicate esters for use in preparing such therapeutic agents have the formula $Si(OR)_4$, wherein each R is an alkyl radical of from 1 to about 6 carbon atoms.

The starting materials can be simply admixed and heated, or they can be reacted in the presence of an inert liquid reaction medium, such as a hydrocarbon.

In many instances, a liquid reaction medium is not required. For example, at reaction temperatures ascorbic acid is soluble (to a usable extent) in tetraethylorthosilicate. On the other hand when both reactants are solids at reaction temperatures, a liquid reaction medium is preferably used. If the reactants are not completely soluble in the liquid, agitation, e.g. stirring, can be used to facilitate contacting the reactants.

The reaction temperature is selected to give a reasonable product yield within a reasonable time. Usually, temperatures above about 65° C. are employed. Temperatures as high as 200° C. or higher can be used.

Preferably, the reaction to prepare therapeutic agents of this invention is conducted at atmospheric pressure. When this expedient is used, it is preferred to use a reaction temperature which is below the boiling point of the lowest boiling reactant in the reaction mixture, and at a temperature which is above the boiling point of the by-product alcohol that is produced in the process. For example, when ascorbic acid is reacted with tetraethylorthosilicate, a convenient reaction temperature is about 155° C. That temperature is slightly below the boiling point of the silicate, and above the boiling point of the ethanol by-product. Such a temperature facilitates removal of unreacted tetraethylorthosilicate from the reaction zone, and thereby assists in isolation of the reaction product.

The reaction zone may be swept with a stream of inert gas if desired, to assist removal of co-product alcohol and/or unreacted starting material.

The reaction temperature is not a truly independent variable, but is at least somewhat dependent upon the other reaction conditions employed. In general, higher reaction temperatures afford shorter reaction times. Furthermore, good mixing of the reactants, and efficient removal of the alcohol co-product help drive the reaction to completion, and thereby lead to shorter reaction periods. In general, the process can be conducted over a reaction period of from about 1 to about 24 hours. The reaction can be conducted in a plurality of stages. For example, the reaction can be conducted at one temperature for an initial reaction period; and thereafter, the temperature can be increased somewhat for a relatively short time, in order to assist reaction of the portion of starting materials which remains after the initial reaction period.

As stated above, a preferred reaction pressure is ambient pressure. However, it will be apparent to a skilled practitioner that sub-atmospheric pressures and super-atmospheric pressures can be employed if desired.

Usually, the products are solid in nature. When a liquid is present in the reaction mixture, the products can be removed therefrom by filtration. Preferably, the reactant mixture is cooled prior to filtering the product. After the product is isolated from the reaction mixture, it can be washed, dried, and subdivided, if desired.

In a preferred embodiment, the starting materials are combined and reacted such that the therapeutic agents of this invention contains at least 2 weight percent, and more preferably from about 10 to about 15 weight percent silicon. Suitable therapeutic agents of this type can be made by reacting one mole of ascorbic acid or other carbohydrate with one mole of a tetraloweralkylorthosilicate, such as tetraethylorthosilicate.

The exact nature of the therapeutic agents of this invention, made by reacting a polyhydroxy compound with a silicon-containing moiety, is not known. Analysis of a typical therapeutic agent of this type (by NMR and infrared) indicates that the reaction product is polymeric in nature. The molecular weight of this type of product, i.e. the degree of polymerization, is difficult to determine since the products are generally insoluble in solvents commonly used in molecular weight determinations. The products can be dissolved in an aqueous medium such as an aqueous acid or aqueous base. However, solution in an aqueous medium causes hydrolysis. Hence, the molecular weight of the products of this invention cannot be determined in aqueous media.

It is believed that the therapeutic agents of this type are not homogeneous; but rather, that they consist of mixtures of various materials made by reaction of the orthosilicate ester and the polyhydroxy compound, e.g. ascorbic acid and/or substituted ascorbic acid.

EXAMPLE 1

A three-necked, round-bottom, Pyrex flask fitted with a mechanical stirrer was employed. One neck was fitted with a condenser so that volatile materials could be retained or removed, as desired. To minimize undesired hydrolysis, a positive nitrogen pressure was employed to prevent moisture entering the system.

A 100 gram portion of ascorbic acid was added to the reaction flask. After mild heating and nitrogen purging, 200 ml of tetraethylorthosilicate was added. The resultant mixture was then heated to 50° C. for two hours, followed by another two hours at 80° C., under vigorous agitation. The resultant mixture was then heated to remove ethanol, and this was followed by tetraethylorthosilicate removal at about 155° C.

The solid product remaining in the flask was cooled to room temperature, and then washed with methanol. The sample was then dried overnight in a vacuum oven, and then subdivided by grinding in a Waring blender.

The product was insoluble or substantially insoluble in organic solvents such as dichloromethane, dimethylsulfoxide (DMSO), acetone, toluene, tetrahydrofuran (THF), and carbon tetrachloride.

The product contained 11 percent silicon as determined by ICP (inductively coupled plasma) atomic absorption spectrometry. Examination by XRD (X-ray diffraction) suggested the presence of ascorbic acid groups within the product. When the diffraction pattern of the product was compared to the diffraction pattern of starting ascorbic acid, an ascorbic acid content of 19 weight percent was determined.

To identify species produced by hydrolysis of the product, a small product sample was slurried in water, under agitation. At various time periods, slurries were withdrawn and filtered through a syringe filter. The siliceous material in the filtrate was then derivatized using hexamethyldisiloxane in the presence of HCl. The trimethylsilyl derivative produced was analyzed by vapor phase chromatography. Results showed only the presence of the trimethylsilyl derivative of orthosilicic acid. This suggests that almost all siliceous material generated by hydrolysis of the sample was orthosilicic acid and/or species that can be converted to orthosilicic acid readily.

Another sample of the product was hydrolyzed under alkaline conditions to determine the amount of ethanol present. A release of ethanol equivalent to 5.8 weight percent of the sample was detected. This amount of ethanol is substantially smaller than the theoretical ethanol release obtained by hydrolysis of tetraethylorthosilicate (88.4 weight percent).

The above procedure can be modified by using a reaction temperature of from about 65° C. to about 200° C. The process can be further modified by using a substituted ascorbic acid, such as those defined above, e.g. co-ascorbic acid derivatives having an ascorbic acid moiety substituted with methyl, ethyl, n-propyl, sec-butyl, n-pentyl, or n-hexyl groups, or being partially esterified with carboxylic acid groups, such as formyl, acetyl, propionyl, or caproyl groups.

The above procedure can be modified by replacing the tetraethylorthosilicate reactant with a material having the formula $Si(OR)_4$, wherein each R is an alkyl group having 1, or from 3 to 6 carbon atoms.

The above procedure can be modified by reacting from 1 to 4 moles of a polyhydroxy compound, e.g. a carbohydrate such as ascorbic acid or substitute ascorbic acid per mole of silicate ester, or by reacting 1 to 4 moles of silicate ester per each mole of ascorbic acid or substituted ascorbic acid, or other polyhydroxy material of the type described above, to produce a material having from 2 weight percent, and more preferably from about 10 to about 15 weight percent silicon.

Following the general procedure described above, the above-mentioned modifications of the procedure in the Example can be conducted by contacting the reactants for a time within the range of from about 1 to about 24 hours.

EXAMPLE 2

Utilizing a reaction vessel of the type described in the previous example, 100 grams of glycerol and 142 grams of tetraethylorthosilicate were reacted by heating at 140° C. for about 3 hours, with stirring. Reaction was stopped after a hard gel was formed, and the agitator was frozen. The gel was transferred to an evaporation dish and placed in a vacuum oven overnight to remove unreacted material. The product had a silicon content of 8.0 percent by weight.

EXAMPLE 3

To a reaction vessel of the type described above was added 42 grams of sucrose. The vessel was then mildly heated, utilizing a nitrogen stream to remove moisture which might have been present in the sucrose. Thereafter, 104 grams of tetraethylorthosilicate was added to the flask. The slurry was heated at reflux for 4 hours, followed by removal of volatile products via distillation. The sucrose/silicate mixture was a heterogeneous system throughout the reaction.

After removal of volatiles in a vacuum oven, the solid product was ground with a Waring blender. Elemental analysis showed a silicon content of 3.13 weight percent.

Following the procedure of Examples 2 and 3, other therapeutic agents of this invention can be produced by reacting a tetraloweralkylsilicate with other carbohydrates of the types discussed above. Generally speaking, it is preferred that the reaction products produced for use as therapeutic agents of this invention have a silicon content of at least 2 weight percent. More preferably, the silicon content is from about 10 to about 15 weight percent.

Above, it was stated that silicon tetracarboxylates can be used as therapeutic agents in this invention. These materials comprise a fourth type of therapeutic agent. They have the formula $Si(OR')_4$, wherein R' is a radical derived from a carboxylic acid. In other words, R' is a carboxyl radical. Therapeutic agents of this type are exemplified by silicon tetraacetate. They can be prepared by reacting a silicon halide (such as silicon tetrachloride or silicon tetrabromide) with a carboxylic acid under conditions which favor the splitting out of co-product hydrohalide, e.g. HCl, or HBr. Residual halogen may be present in the silicon carboxylates so produced. Preferably, at least one-half of the silicon valences in the carboxylate are satisfied by bonding to carboxy groups rather than to halogen.

In the carboxylates, the radicals depicted by R' in the above formula may be alike or different. Preferably, they are the same. The tetracarboxylates used as therapeutic agents in this invention may be produced from the carboxylic acids and anhydrides, such as those described below.

Amino acids such as L-aspartic acid and glutamic acid can be used in this invention. Unlike glycine and similar acids in which each carboxyl group has an amino group on an alpha carbon, aspartic and glutamic acid has a carboxyl group which does not have an alpha amino group. This isolated carboxyl is non-zwitterionic, and therefor L-aspartic acid and similar materials with an isolated carboxyl comprise a preferred class of organic acids. The acid may be ascorbic acid, or some other acidic substance in which the acid function is derived from groups or radicals other than the carboxylic acid group. Alternatively, the acid may be a monobasic, dibasic, tribasic or tetrabasic carboxylic acid. Acids of this type include acetic acid, trimethylacetic acid, lactic acid, benzoic acid, malonic acid, tartaric acid, gluconic acid, citric acid, and the like. Preferably, the acid has three to six carbons such as propionic, pivalic, malic, malonic, maleic, succinic, butyric, valeric, fumaric and glutaric acids.

Thus, the acids employed to prepare silicon carboxylates for use in this invention may be selected from acids having one of the following formulas: R'-COOH,R''-(COOH)$_2$, and R'''(COOH)$_3$. In these molecular formulas R', R'' and R''' are organic radicals, e.g. hydrocarbyl radicals, i.e. radicals which are solely composed of carbon and hydrogen. The radicals represented by R', R'' and R''' may be cyclic or acyclic, straight or branched chain, saturated or unsaturated. The cyclic radicals may be aromatic or non-aromatic. In the above formulas, the radicals R', R'', and R'''may also be selected from hydroxy-substituted hydrocarbyl radicals. Preferably, the acids contain up to about 10 carbon atoms.

The exact nature or molecular configuration of the acid adjuvant selected is not critical so long as the acid is appreciably soluble in gastric fluid in the animal being treated and is pharmaceutically acceptable.

The acids may contain other elements than carbon, hydrogen and oxygen; they may contain a halogen, e.g. fluorine, chlorine or bromine, or sulphur, phosphorus and the like.

Other examples of acids that may be used include decanoic, undecylenic, salicylic, benzenesulfonic, camphorsulfonic, p-chlorobenzensulfonic, 4-methylbicyclo[2.2.2]oct-2-ene-1-carboxylic, cyclopentanepropionic, 1,2-ethanedisulfonic, ethanesulfonic, o-(4-hydroxybenzyl)benzoic, 2-hydroxyethane-sulfonic, methanesulfonic, dodecylsulfonic, stearic, 2-naphthylenesulfonic, 3-phenylpropionic, p-toluenesulfonic, gluconic, pantothenic, palmitic, hippuric, mandelic, and caproic acid, and the like.

The following illustrates the use of the bone growth stimulating agents of this invention.

GENERAL PROCEDURE

Egg Preparation

An incubation study was conducted in which trace amounts of organosilicates were injected into hatching eggs the day after day 7 of incubation. The hole through which the injection took place was sealed with wax and the eggs were set in an incubator and hatched out. Aqueous suspensions of organosilicate were prepared, and 0.1 ml portions of suspensions were injected into each egg. Groups of 150 eggs of approximately equal weight were used for each treatment. Doses were selected to contain 0, 7.92, 15.8, or 31.6 micrograms of silicon in each egg.

The water suspensions of zeolite A were prepared with sterile water, i.e. water free of bacteria or other harmful substances which might have a deleterious effect on the chick embryos.

METHODS

Egg Weights

Egg weights were determined on an electronic balance (American Scientific Products (ASP) Model DTL 25006) to the nearest 0.1 g before incubation.

Chick Weights

Chicks were weighed to the nearest 0.1 gram on an electronic balance (ASP Model DTL 25006).

Chick Weight/Egg Weight Ratio

Weights of all unhatched eggs were removed from the initial egg weight data set. The ratio of hatching chick weight to egg weight was then calculated for each treatment group.

Bone Length and Dry Weight

The right tibiotarsus was removed from each chick. The tibiotarsi were placed in boiling water for approximately 2 minutes to facilitate removal of tissue and cartilage caps. Afterwards, tibiotarsus length (mm) was measured with a Vernier caliper (Sargent-Welch, S-44775-10). The tibiotarsi were extracted for 16 hours with petroleum ether in a Goldfisch Fat Extractor (Labconco, 35001). The bones were then allowed to air dry overnight. Afterwards, the tibiotarsi and crucibles were dried in a forced-draft oven at 160° C. for 1 hour, cooled for 30 minutes in dessicators, and then weighed on an analytical balance (Mettler, H315) to the nearest 0.1 mg.

Experiment A

This experiment was designed to determine the effect of the organosilicates, tetraethylsilicate and silicon tetraacetate, on skeletal development. The following table lists the mean values for chick weight, egg weight, chick:egg weight ratio, tibial length, and bone dry weight for chicks hatched from broiler eggs having mean weights in each group between 67.25 and 69.02 grams. Uninjected, and water injected eggs were used for controls.

| | Example A | | | | | |
|---|---|---|---|---|---|---|
| Treatment No. | 1 | 2 | 3 | 4 | 5 | 6 |
| Test Article | Untreated | Water | STEO* | STEO | STEO | STA** |

-continued

| | Example A | | | | | |
|---|---|---|---|---|---|---|
| Treatment No. | 1 | 2 | 3 | 4 | 5 | 6 |
| Dose: Silicon micrograms per egg | 0 | 0 | 7.92 | 15.8 | 31.7 | 15.8 |
| Chick Weight (g) | 47.21 | 45.99 | 46.64 | 45.70 | 47.36 | 46.07 |
| Egg Weight (g) | 68.07 | 68.80 | 67.97 | 67.74 | 69.02 | 67.25 |
| Chick Wt./Egg Wt. | 0.6938 | 0.6686 | 0.6865 | 0.6746 | 0.6859 | 0.6845 |
| Tibiotarsus Length (mm) | 2.693 | 2.718 | 2.711 | 2.729 | 2.781 | 2.747 |
| Tibiotarsus Dry Wt. (g) | 0.05150 | 0.05580 | 0.05412 | 0.05257 | 0.06113 | 0.05719 |

*STEO = Tetraethylorthosilicate.
**STA = Silicon tetraacetate.

To evaluate the effect on chick development, the ratio of chick weight to egg weight shows that all treatments lead to a heavier chick per weight of egg, compared to water injection alone. This is taken to mean that more of the shell mineral is transferred from the shell to the skeleton in silicate treated animals. When compared to uninjected eggs, the injection process itself however seems to reduce the weight of chick. (It will be seen in Experiment B, however, that this is not a uniform pattern.)

Comparison of tibial length for both uninjected and water injected control shows that treatment with organosilicates uniformly results in longer tibia. A similar pattern in the bone dry weight is found comparing uninjected controls with organosilicate treated weights. Water injection alone also seems to increase bone dry weight, and birds in treatment group 3 and 4 were not superior to water injection alone. (The increase in bone dry weight due to water injection alone may be an artifact.) Bone dry weight in treatment 5 and 6, however, were superior to the water injected controls.

Experiment B

This experiment was designed to evaluate the effect of various organosilicate complexes on skeletal development as in Experiment A. Similar procedures and measurements to that in the preceding experiment were used here as well. In this experiment, however, the mean egg weights in each treatment ranged from 55.03 to 56.44 grams. The results of this experiment are found in the following table.

| | Example B | | | | | |
|---|---|---|---|---|---|---|
| Treatment No. | 1 | 2 | 3 | 4 | 5 | 6 |
| Test Article | Water | SUC-Si* | SUC-Si | ASC-Si** | ASC-Si | GLY-Si** |
| Dose: Silicon micrograms per egg | 0 | 15.8 | 31.6 | 15.8 | 31.6 | 31.6 |
| Chick Weight (g) | 36.56 | 37.24 | 38.22 | 37.65 | 37.86 | 37.88 |
| Egg Weight (g) | 55.03 | 55.53 | 56.18 | 56.45 | 55.77 | 55.60 |
| Chick Wt./Egg Wt. | 0.6691 | 0.6705 | 0.6800 | 0.6667 | 0.6791 | 0.6815 |
| Tibiotarsus Length (mm) | 2.500 | 2.549 | 2.524 | 2.562 | 2.461 | 2.487 |
| Tibiotarsus Dry Wt. (g) | 0.04038 | 0.04378 | 0.04350 | 0.04456 | 0.04183 | 0.04203 |

*SUC-Si = Reaction Product of Sucrose and Tetraethylorthosilicate.
**ASC-Si = Reaction Product of Ascorbic Acid and Tetraethylorthosilicate.
***GLY-Si = Reaction Product of Glycerin and Tetraethylorthosilicate.

As in the previous experiment, the chick weight/egg weight ratio is consistently greater in treated compared to water injected eggs. Tibiatorsal length is also generally greater in the treated birds except in the high dose ascorbate-Si complex treated birds (treatment 5). In this instance, we may have reached a toxic dose level. In addition, silicate treatment results in a consistently greater tibial dry bone weight when compared with water injected control, a pattern which appears superior to that of Treatments 3 and 4 of the previous Experiment A.

The above results are indicative of the type of improvement in bone length or mass obtained by treating fertile bird eggs with up to about 35 micrograms of silicon as a therapeutic agent of this invention. Similar results are obtained if the eggs are sprayed or soaked with solutions or suspensions of the therapeutic agent, and the concentration of the agent in the aqueous mixture utilized is from about 50 to about 2000 ppm.

Results similar to the above are obtained when using domestic fowl other than chickens; e.g. turkeys, ducks, geese, and the like. Eggs from avian species other than domestic poultry may also benefit from treatment according to the method of this invention. Among these are included bob white quail and pheasants grown for release in game preserves, pigeons grown for squab delicacy or racing sport, and other birds grown for show birds and for bird fanciers, e.g. parakeets.

It is suggested that this invention can be extended to use with other non-domesticated avian species. More and more frequently, breeding pairs, eggs, and immature young of rare and/or endangered species are being raised and managed in programs directed to prevention of species extinction. It is believed that good results of the type described above could be obtained by treating eggs of such birds with one or more of the bone growth stimulating agents of this invention described above, in order to improve the quality, health, weight, or strength of chicks hatched from the treated eggs. Thus, this invention may be useful in developing larger, more stable populations of avian species that might otherwise become extinct.

It is also suggested that eggs of endangered reptilian species, e.g. turtles, may also be treated according to the method of this invention.

Furthermore, it is suggested that the bone growth stimulating agents of this invention can be administered (to the fertile egg being treated) admixed with an acidifying agent. Such agents are exemplified by pharmaceutically acceptable organic acids of the type mentioned above. Such acid adjuvants which may be admixed with the therapeutic agents of this invention are also described in Application Ser. No. 153,456, filed Feb. 8, 1988. Both of us, with another, are co-inventors of that application. The description of the acidifying agents set forth in Application Ser. No. 153,456, is incorporated by reference herein, as if fully set forth.

The stimulation in embryonic bone growth resulting from the method of this invention suggests that the therapeutic agents disclosed above can be used to treat osteoporosis in humans and related diseases in warm blooded vertebrates. For example, the above results suggest that the therapeutic agents of this invention can be used to treat post-menopausal osteoporosis in human females, steroid-induced osteoporosis, and hypogonadotropic osteoporosis in human males and females.

With the above-detailed description of this invention, a skilled practitioner can make many modifications of the embodiments described without departing from the spirit and scope of the dependent claims.

We claim:

1. A method for stimulating the growth of bone tissue in poultry, said method comprising treating a fertile bird egg prior to the hatching of a chick therefrom with (i) a small but effective amount of a physiologically acceptable organic silicon compound in which silicon is solely bonded to oxygen or halogen, preferably chlorine or bromine, such that not less than one-fourth of the valences of silicon are satisfied by bonding to oxygen, or (ii) silicic acid produced by said bird egg from an effective amount of said organic silicon compound administered to said egg.

2. The method of claim 1, wherein said organic silicon compound is a tetraorganoorthosilicate having the formula $Si(OR)_4$ wherein each organo radical represented by R has from 1 to about 6 carbon atoms, and is alike or different, and solely composed of carbon and hydrogen.

3. The method of claim 2, wherein said organic silicon compound is a tetraethylorthosilicate.

4. The method of claim 1, wherein the silicon is solely bonded to oxygen present in a carbohydrate.

5. The method of claim 4, wherein said carbohydrate is glycerin.

6. The method of claim 4, wherein said carbohydrate is glucose.

7. The method of claim 4, wherein said carbohydrate is sucrose.

8. The method of claim 4, wherein said carbohydrate is ascorbic acid.

9. The process of claim 1, wherein said organic silicon compound is a silicon tetracarboxylate.

10. The method of claim 9, wherein said compound is silicon tetraacetate.

11. The method of claim 1, wherein the poultry chick is selected from the group consisting of chickens, turkeys, and other domestic fowl.

* * * * *